US012091653B2

(12) United States Patent
Long et al.

(10) Patent No.: US 12,091,653 B2
(45) Date of Patent: Sep. 17, 2024

(54) **STRAIN OF *GLUTAMICIBACTER*, ORIGINATING FROM INSECTS, CAPABLE OF EFFICIENTLY DEGRADING BIFENTHRIN**

(71) Applicant: Anhui Agricultural University, Hefei (CN)

(72) Inventors: Yanhua Long, Hefei (CN); Xiayu Li, Hefei (CN); Ting Fang, Hefei (CN); Hao Gui, Hefei (CN); Meiqi Wang, Hefei (CN); Haiyue Wang, Hefei (CN); Yanru Bao, Hefei (CN); Anqi Shi, Hefei (CN); Yuhan Pan, Hefei (CN); Linlin Zhou, Hefei (CN); Xiaochun Wan, Hefei (CN); Yunqiu Yang, Hefei (CN)

(73) Assignee: ANHUI AGRICULTURAL UNIVERSITY, Hefei (CN)

( * ) Notice: Subject to any disclaimer, the term of this patent is extended or adjusted under 35 U.S.C. 154(b) by 0 days.

(21) Appl. No.: 18/526,264

(22) Filed: Dec. 1, 2023

(65) Prior Publication Data

US 2024/0101956 A1    Mar. 28, 2024

(30) Foreign Application Priority Data

Jul. 3, 2023 (CN) .......................... 202310815370.X (51) Int. Cl.
| | | |
|---|---|---|
| *C12N 1/20* | (2006.01) | |
| *C05F 11/08* | (2006.01) | |
| *C05G 3/40* | (2020.01) | |
| *C12R 1/01* | (2006.01) | |

(52) U.S. Cl.
CPC .............. *C12N 1/205* (2021.05); *C05F 11/08* (2013.01); *C05G 3/40* (2020.02); *C12R 2001/01* (2021.05)

(58) Field of Classification Search
CPC ........ C12N 1/205; C12R 2001/01; B09C 1/10
See application file for complete search history.

(56) References Cited

PUBLICATIONS

Chen et al. Microbial detoxification of bifenthrin by a novel yeast and its potential for contaminated soils treatment; PLoS One 2012; 7(2):e30862. doi: 10.1371/journal.pone.0030862. Epub Feb. 13, 2012. (Year: 2012).*

* cited by examiner

*Primary Examiner* — Louise W Humphrey
*Assistant Examiner* — Alexander M Duryee
(74) *Attorney, Agent, or Firm* — IPRO, PLLC

(57) ABSTRACT

The present disclosure discloses a novel strain of Glutamicibacter, derived from insects, which efficiently degrades bifenthrin, belonging to the field of microbial strains. The Glutamicibacter CCTCC NO: M20221445 of the present disclosure was isolated from the intestinal tract of bifenthrin-resistant *Ectropis grisescens* Warren larvae. It exhibits unique genomic characteristics, growth and phenotypic traits, physiological and biochemical characteristics, as well as the ability to utilize and degrade bifenthrin efficiently. Specifically, it can effectively degrade bifenthrin. Based on phenotypic features, physiological and biochemical characteristics, chemical composition, and molecular biology-based polyphasic classification, Glutamicibacter CCTCC NO: M20221445 is identified as a new species. This bacterium possesses the capability to efficiently degrade bifenthrin, laying the foundation for biological control of *E. grisescens* and offering new microbial resources to address pesticide residue problems.

5 Claims, 8 Drawing Sheets

Specification includes a Sequence Listing.

SEQUENCE LISTING

```
Sequence total quantity: 3
SEQ ID NO: 1          moltype = DNA  length = 1414
FEATURE               Location/Qualifiers
source                1..1414
                      mol_type = other DNA
                      organism = synthetic construct
SEQUENCE: 1
acgtcaccat tcgacgactc cccccacaca aggtggttag gccatcggct tcgggtgtta    60
ccaactttcg tgacttgacg ggcggtgtgt acaaggcccg ggaacgtatt caccgcagcg   120
ttgctgatct gcgattacta gcgactccga cttcatgggg tcgagttgca gacccaatc    180
cgaactgaga ccggcttta gggattagct ccacctcaca gtatcgcaac ccattgtacc    240
ggccattgta gcatgcgtga agcccaagac ataagggca tgatgatttg acgtcatccc    300
caccttcctc cgagttgacc ccggcagtct cccatgagtc cccaccacta cgtgctggca   360
acatggaacg agggttgcgc tcgttgcggg acttaaccca acatctcacg acacgagctg   420
acgacaacca tgcaccacct gtgaaccagc cccgaaggga aagaccatct ctgatccggt   480
ctggcacatg tcaagccttg gtaaggttct tcgcgttgca tcgaattaat ccgcatgctc   540
cgccgcttgt gcgggccccc gtcaattcct ttgagtttta gccttgcggc cgtactcccc   600
aggcggggca cttaatgcgt tagctacggc gcggaaaacg tggaatgtcc cccacaccta   660
gtgcccaacg tttacggcat ggactaccag ggtatctaat cctgttcgct ccccatgctt   720
tcgctcctca gcgtcagtaa atgcccagag acctgccttc gccatcggtg ttcctcctga   780
```

-continued

```
tatctgcgca tttcaccgct acaccaggaa ttccagtctc ccctacatca ctctagtctg  840
cccgtaccca ccgcagatcc gaggttgagc ctcggacttt cacggcagac gcgacaaacc  900
gcctacgagc tctttacgcc caataaatcc ggataacgct tgcgccctac gtattaccgc  960
ggctgctggc acgtagttag ccggcgcttc ttctgcaggt accgtcactc tcgcttcttc  1020
cctactgaaa gaggtttaca acccgaaggc cgtcatccct cacgcggcgt cgctgcatca  1080
ggcttgcgcc cattgtgcaa tattccccac tgctgcctcc cgtaggagtc tgggccgtgt  1140
ctcagtccca gtgtggccgg tcaccctctc aggccggcta cccgtcgtcg ccttggtgag  1200
ccattacctc accaacaagc tgataggccg cgagtccatc ccccaccgat aaatctttca  1260
acaacccacc atgcggtaag aagtcatatc cggtattaga cccagtttcc cgggcttatc  1320
ccaaagtcgg gggcaggtta ctcacgtgtt actcacccgt tcgccactaa tccaccctgc  1380
aagcagggct tcatcgttcg actgcatggt agcg                              1414

SEQ ID NO: 2            moltype = DNA  length = 20
FEATURE                 Location/Qualifiers
source                  1..20
                        mol_type = other DNA
                        organism = synthetic construct
SEQUENCE: 2
agagtttgat cctggctcag                                              20

SEQ ID NO: 3            moltype = DNA  length = 19
FEATURE                 Location/Qualifiers
source                  1..19
                        mol_type = other DNA
                        organism = synthetic construct
SEQUENCE: 3
ggttaccttg ttacgactt                                               19
```

STRAIN OF *GLUTAMICIBACTER*, ORIGINATING FROM INSECTS, CAPABLE OF EFFICIENTLY DEGRADING BIFENTHRIN

REFERENCE TO SEQUENCE LISTING

The instant application contains a Sequence Listing in XML format as a file named "3054-PC230002A.xml", created on Nov. 29, 2023, of 5267 bytes in size, and which is hereby incorporated by reference in its entirety.

TECHNICAL FIELD

This disclosure relates to a novel strain of Glutamicibacter, originating from insects, capable of efficiently degrading bifenthrin, and belongs to the field of microbial species.

BACKGROUND

China's tea tree cultivation is diverse, with a continually expanding tea plantation area, showing a promising trend of sustained and stable growth. However, *Ectropis grisescens* Warren, as a type of leaf-feeding pest, poses significant economic losses to tea farmers. Consequently, farmers resort to using chemical pesticides like bifenthrin to control *E. grisescens*. Bifenthrin is a moderately toxic Pyrethroid pesticide. Nevertheless, the long-term usage of chemical pesticides has increasingly manifested in the form of agricultural residues. This not only exacerbates environmental pollution but also contributes to the development of resistance in *E. grisescens* against bifenthrin.

The insect gut harbors a rich reservoir of microbial resources. Insects provide a relatively unique and stable environment with their gut for these microorganisms. Simultaneously, gut microbiota in insects provide nutrients, assist the immune system, and contribute to insect development and metabolism. The metabolic activities and byproducts of insect gut microbiota can help the host insect adapt to various environmental stresses. Current research suggests that insect gut symbionts can facilitate the host's utilization of exogenous nutrients, aid in the degradation of food, and provide essential nutrients lacking in the host's diet. Moreover, some symbionts can assist in inter- and intra-species communication and even promote the growth and development of their host, influencing the host's lifespan. In recent years, as research on gut microbiota has deepened, it has become evident that there is a connection between symbiotic bacteria and insect resistance. This is primarily manifested in how insect symbionts can directly metabolize toxic substances or indirectly mediate the expression of detoxifying enzymes or related genes in the host, thereby enhancing the insect's resistance to toxins.

Currently, there have been no reported studies regarding the relationship between the gut symbionts of *E. grisescens* and host insect resistance. If efficient microorganism of bifenthrin degrading can be screened and isolated from the gut of *E. grisescens*, this could offer a novel approach and microbial resource for addressing the issue of agricultural residues.

SUMMARY

To address at least one of the aforementioned issues, this disclosure isolates a novel strain of Glutamicibacter from the gut of *E. grisescens* larvae, which demonstrates a high-efficiency capability for degrading bifenthrin. Additionally, this disclosure conducts a comprehensive identification of this strain through molecular biology, physiological and biochemical analysis, chemical component analysis, and phenotype characterization. It is anticipated that this microbial perspective will lay a foundation for environmentally friendly pest control in *E. grisescens* and provide new insights and microbial resources for solving the problem of agricultural residues.

The disclosure provides a strain of Glutamicibacter, denoted as Eg-H, which possesses high-efficiency bifenthrin-degrading capabilities. This strain was deposited on Sep. 16, 2022, at the China Center for Type Culture Collection (CCTCC) under the accession number CCTCC NO: M20221445.

The new strain of Glutamicibacter, designated as CCTCC NO: M20221445, exhibits the following characteristics:

(1) Genome Features:

The strain's genome displays an average nucleotide identity (ANI) of 82.78% with the most closely related, well-characterized species in the Glutamicibacter genus, marking it as a novel species. The genome has a length of 3,189,534 base pairs, containing 3,362 genes with an average gene length of 948.70 base pairs and its GC content is 55.78%. The strain contains 19 rRNA genes, 64 tRNA genes and 1 sRNA gene.

(2) Growth and Phenotypic Characteristics:

The strain is Gram-positive, facultative anaerobic, non-motile, and non-sporulating, with a rod-shaped bacterial morphology. The bacterial cells are shorter in the absence of bifenthrin but become elongated in its presence. When cultured on LB solid medium at 37° ° C. for two days, the colonies are yellow, smooth, circular, and have a regular edge. Typically, colony diameters range from 0.5 to 0.6 mm. The strain grows within a temperature range of 15-40° C., with its optimal growth temperature at 30° C. It can tolerate salt concentrations between 0-10% (w/v), with the optimal salt concentration for growth being 2%. The strain's growth pH range is 5-10, with the most favorable growth pH at 8.0.

(3) Physiological and Biochemical Characteristics:

The strain produces valine arylaminase and cysteine arylaminase.

The strain can ferment L-arabinose, D-xylose, D-galactose, D-glucose, D-fructose, rhamnose, inositol, esculin ferric citrate, D-cellobiose, D-maltose, D-sucrose, inulin, D-raffinose, starch, glycogen, D-ribose, etc., producing acid as metabolic products.

The strain can utilize various carbon sources, including dextrin, D-arabitol, D-fructose, D-glucuronic acid, α-D-glucose, maltose, D-raffinose, D-ribose, sucrose, L-lactic acid, L-malic acid, propionic acid, D-alanine, L-alanine, glutamic acid, pyroglutamic acid, serine, glycerol, and inosine.

The strain exhibits enzymatic activities including catalase, cysteine arylaminase, and valine arylaminase.

(4) Utilization and Degradation Characteristics of Bifenthrin:

The strain can grow in a basal salt medium with bifenthrin as the sole carbon source.

When the strain cultured in liquid media containing 6 mg/L of bifenthrin for 48 hours, the degradation efficiency of bifenthrin can reach 84.75%.

When the initial concentration of bifenthrin in the medium is less than or equal to 60 mg/L, Glutamicibacter sp. Eg-H exhibits a degradation rate of bifenthrin ranging from 75.78% to 85%. However, when the initial concentration of bifenthrin is increased to 100 mg/L, the degradation rate decreases to 49.89%, and at a high initial concentration of 200 mg/L, the degradation rate is 16.49%.

The initial degradation products of bifenthrin of the strain exhibit either no toxicity or very low toxicity to *E. grisescens* larvae.

The disclosure further provides a composition containing Glutamicibacter CCTCC NO: M20221445. This composition can be a microbial agent, microbial fertilizer, or *E. grisescens* feed.

In an embodiment, the composition contains a minimum of $10^7$ CFU (colony-forming units) of Glutamicibacter CCTCC NO: M20221445 per gram or milliliter.

In an embodiment, the microbial agent can be a liquid microbial agent or a solid microbial agent. It may include freeze-dried bacterial cells or immobilized cells.

In an embodiment, the liquid microbial agent is prepared by activating Glutamicibacter CCTCC NO: M20221445 and inoculating it into LB liquid culture.

In an embodiment, the solid microbial agent is a freeze-dried powder containing Glutamicibacter CCTCC NO: M20221445.

In an embodiment, the microbial agent may also contain other additives, such as protectants; these protectants could include maltodextrin, starch, glycerol, dimethyl sulfoxide (DMSO), and others.

The disclosure further provides a method for degrading bifenthrin. This method involves adding Glutamicibacter CCTCC NO: M20221445 or a microbial agent containing Glutamicibacter CCTCC NO: M20221445 to a system containing bifenthrin.

In an embodiment, the system containing bifenthrin can be tea plant leaves, soil, or similar environments.

In an embodiment, the concentration of bifenthrin in the system can range from 0 to 200 mg/L.

In an embodiment, the concentration of bifenthrin can range from 5 to 100 mg/L, optionally within the range of 5 to 60 mg/L.

In an embodiment, the degradation method involves inoculating Glutamicibacter CCTCC NO: M20221445 into the system containing bifenthrin and cultivating for a specified period, which can range from 12 to 72 hours, optionally 36 to 48 hours.

In an embodiment, Glutamicibacter CCTCC NO: M20221445 is inoculated into a system containing bifenthrin at a concentration of 2% to 7% (v/v).

The disclosure further provides a microbial fertilizer containing Glutamicibacter CCTCC NO: M20221445. This microbial fertilizer can be applied to degrade bifenthrin residues in the soil.

In an embodiment, the microbial fertilizer is a slow-release type containing, potassium humate, urea, magnesium sulfate, potassium sulfate, Glutamicibacter CCTCC NO: M20221445 microbial agent, glutinous rice starch, ammonium chloride, ammonium dihydrogen phosphate, and sodium alginate.

In an embodiment, the microbial fertilizer is a soil conditioner microbial fertilizer, composed of the following weight percentages of materials: Glutamicibacter CCTCC NO: M20221445 microbial agent (40-45%), potassium humate (25-30%), amine azide (2-3%), yeast extract (5-6%), chitosan (5-6%), sodium humate (4-6%), seaweed extract (4-6%), and complex protease (2-3%).

The disclosure further provides a preparation for increasing the bifenthrin resistance of *E. grisescens*, containing Glutamicibacter CCTCC NO: M20221445. Optionally, this preparation can be a feed.

The Glutamicibacter CCTCC NO: M20221445 from this disclosure can efficiently degrade bifenthrin, thereby enhancing the bifenthrin resistance of *E. grisescens*. This strain can be used to analyze the relationship between bifenthrin resistance and Intestinal symbiotic bacteria of *E. grisescens*, providing a theoretical foundation and control targets for the biological control of *E. grisescens*, and offering new microbial resources for solving the issue of agricultural residues.

Glutamicibacter CCTCC NO: M20221445, isolated from the gut of bifenthrin-resistant *E. grisescens* larvae. Using a basal salt medium with bifenthrin as the sole carbon source, the strain was identified by 16S rDNA sequence. The sequencing results indicated a full-length sequence of 1414 base pairs (as shown in SEQ ID NO:1). A Maximum-Likelihood (ML) phylogenetic tree based on 16S rDNA sequences placed Glutamicibacter sp. Eg-H within the Glutamicibacter genus, forming a separate branch and closely related to two reference strains, Glutamicibacter mishrai S5-52$^T$ and Glutamicibacter halophytocola KLBMP 5180$^T$, with 98.93% and 98.16% similarity, respectively.

Glutamicibacter sp. Eg-H was preliminarily identified as a Glutamicibacter species (Glutamicibacter) based on 16S rDNA sequencing.

Using five reference strains with the closest homology in the phylogenetic tree, Glutamicibacter mishrai S5-52$^T$, Glutamicibacter halophytocola KLBMP 5180$^T$, Glutamicibacter nicotianae NBRC 14234$^T$, Glutamicibacter arliaitensis Re117$^T$, and Glutamicibacter uratoxydans NBRC 15515$^T$ as reference strains. According to «Manual for Identification of Common Bacterial Systems», polyphasic approach was applied to detect morphological characteristics, growth traits, physiological and biochemical characteristics, polar lipid composition, quinone types, fatty acid composition, genomic analysis, and DNA(G+C) content. Additionally, enzyme activity and carbon-nitrogen source utilization were tested using standard methods. The combined data analysis from phenotypic, physiological, biochemical, chemical classification, and DNA-DNA hybridization confirmed that Glutamicibacter sp. Eg-H is a new species within the Glutamicibacter genus.

Beneficial Effects

The Glutamicibacter strain CCTCC NO: M20221445, originating from the intestines of resistant *E. grisescens*, possesses unique genomic characteristics, growth and phenotypic traits, physiological and biochemical features, and the ability to utilize and degrade bifenthrin. Through taxonomical identification, the strain CCTCC NO: M20221445 has been classified as a new species.

The Glutamicibacter strain CCTCC NO: M20221445 can efficiently degrade bifenthrin and can be formulated into microbial agents or microbial fertilizers. It can be used for the degradation of bifenthrin in systems such as tea tree leaves and soil. Furthermore, the degradation byproducts of the strain have been found to be non-toxic or very low in toxicity to *E. grisescens* larvae. This strain can be used in the production of feed to enhance the bifenthrin resistance of *E. grisescens*.

This invention provides a foundation for the biological control of *E. grisescens* and offers a new microbial resource to address pesticide-related issues.

Collection of Biological Materials

The Glutamicibacter strain, taxonomically named as Glutamicibacter sp. Eg-H, was deposited at the China Center for Type Culture Collection (CCTCC) on Sep. 16, 2022. The deposit was made at Wuhan University, Wuhan, China, and the strain was assigned the deposit number CCTCC NO: M 20221445.

DETAILED DESCRIPTION

Below are the formulations of the culture media and reagents mentioned in the provided examples:

1. Saponification Reagent:
    Dissolve 45 g of sodium hydroxide (analytical grade) in 150 mL methanol (HPLC grade) and 150 ml deionized distilled water. Mix water and methanol, then stir while adding sodium hydroxide until it's fully dissolved.
2. Methylation Reagent:
    Mix 325 mL of 6N hydrochloric acid with 275 mL methanol (HPLC grade). Add the acid to methanol while stirring.
3. Extraction Reagent:
    Mix 200 ml of hexane (HPLC grade) with 200 mL ethyl ether (HPLC grade).

4. Bifenthrin Stock Solution:
    Dissolve 0.121 g bifenthrin purity standard sample (99.1% purity, from Beijing Northern Weiye Measurement Technology Research Institute) in 30 mL acetone. Add Tween 20 in a 1:1.5 weight ratio relative to the bifenthrin powder, then bring the volume to 100 ml with acetone to get a 12 g/L bifenthrin emulsion. This forms the bifenthrin stock solution, which can be diluted as needed.
5. PBS Buffer (10 mmol/L, pH 7.4):
    Dissolve KCl 0.02 g, NaCl 0.8 g, $KH_2PO_4$ 0.024 g, $Na_2HPO_4 \cdot 12H_2O$ 0.29 g. in distilled water to a total volume of 50 mL. Adjust pH to 7.4, and then dilute with distilled water to a final volume of 100 mL.
6. LB Liquid Culture Medium:
    Dissolve 10 g peptone, 5 g yeast extract, and 10 g NaCl in water and bring the volume to 1 L.
7. LB Solid Culture Medium:
    Dissolve 10 g peptone, 5 g yeast extract, 10 g NaCl, and 16 g agar in water and bring the volume to 1 L.
8. Basic Salt Culture Medium:
    In a flask, dissolve $(NH_4)_2SO_4$ 20 g, $MgSO_4 \cdot 7H_2O$ 2 g, ($CaCl_2$) 0.1 g, $FeSO_4 \cdot 7H_2O$ 0.01 g, $Na_2HPO_4 \cdot 12H_2O$ 15 g, and $KH_2PO_4$ 15 g in water and bring the volume to 1 L to make a mother solution. Store in a fridge. When needed, dilute tenfold to prepare the Minimal Salt Medium (MSM). For solid culture medium, add 1.6% agar.
9. MSM Medium with Bifenthrin:
    Mix 125 μl of the above bifenthrin stock solution with 250 ml sterile MSM to get a medium with 6 mg/L bifenthrin concentration. For solid media, add 16 g agar. For other concentrations of bifenthrin, dilution can be adjusted similarly.
10. Sterile Artificial Feed:
    In a 250 ml beaker, mix 12 g wheat germ, 4.5 g soybean powder, 2 g sucrose, 2 g agar, 0.5 g Wesson's salt, 0.25 g naphthyl acetate, 0.15 g sorbic acid, 0.1 g cholesterol, 0.05 g inositol, and 70 mL pure water. Stir well, then sterilize at 115° C. for 30 minutes. After sterilization, cool to around 60° C. Separately, mix 0.2 g vitamin C, 0.05 g choline chloride, 0.2 g yeast powder, and dilute with 8 mL pure water. Filter-sterilize using a 0.22 μm membrane, then combine with the above mixture. Stir thoroughly. Store the prepared sterile artificial feed at −20° C.

Example 1: Observation of Morphology of Glutamicibacter sp. Eg-H 1.1 Strain Source The strain Glutamicibacter sp. Eg-H was obtained from the intestinal samples of *E. grisescens* larvae exhibiting resistance. The entire gut was aseptically removed from a resistant strain of *E. grisescens* larva and placed into a homogenizer. It was then thoroughly homogenized with 1 mL of sterile PBS buffer. The homogenized liquid was diluted 105 times, and 50 μL of the dilution was spread on media containing the relevant drug. Three replicates were used for each group. The cultures were incubated at 37° C. in a biochemical incubator. Single colonies were sequentially subcultured three times onto fresh media containing the appropriate drug and LB solid culture medium. The purified strains were stored in 20% glycerol at −80° C. for later use. Among these strains, Glutamicibacter sp. Eg-H is the strain relevant to this disclosure.

1.2 Phenotypic and Growth Characteristics of the Strain

The strain obtained in section 1.1 was inoculated onto LB solid culture medium and incubated at 37°C for 24 hours.

Figure 1:
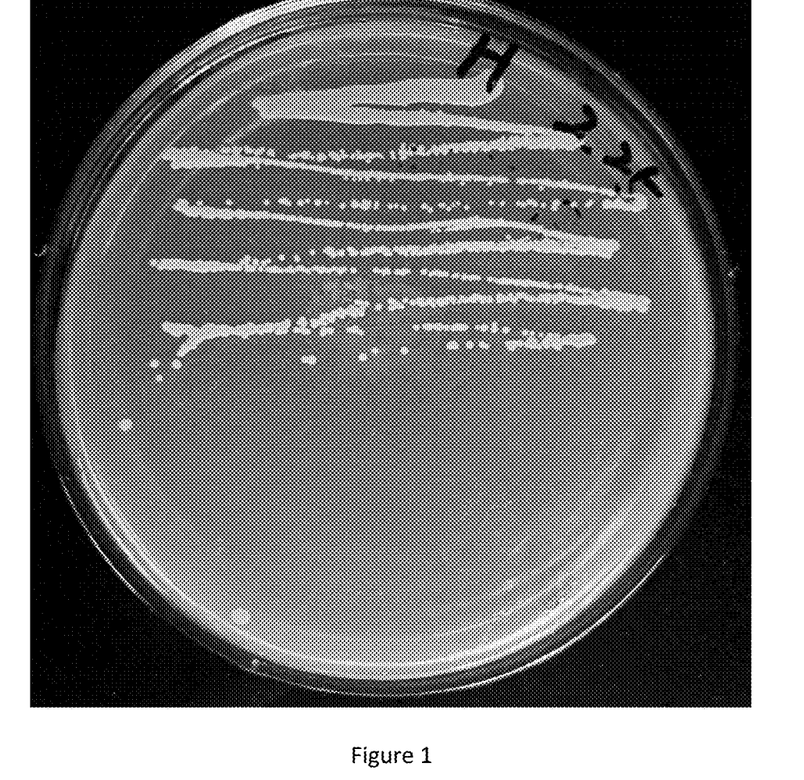
FIG. 1 shows the colony morphology characteristics of the Glutamicibacter sp. Eg-H strain.
Figure 2:
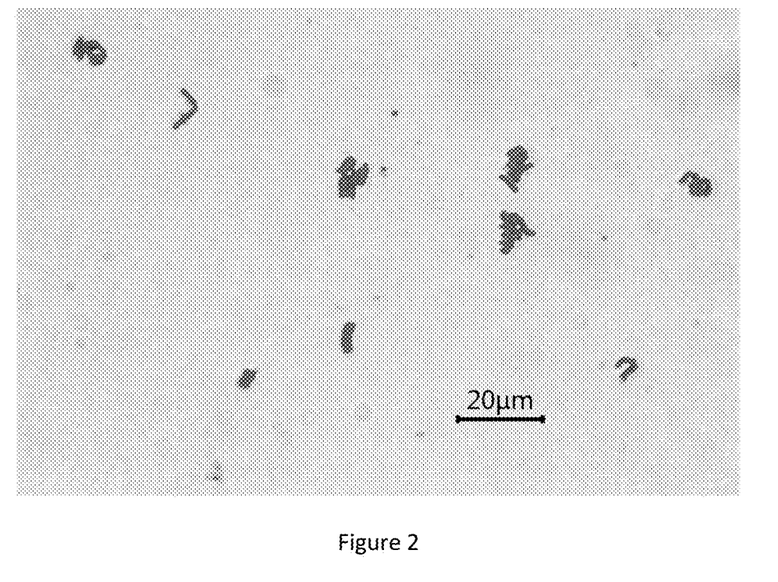
FIG. 2 shows the Gram staining of Glutamicibacter sp. Eg-H strain.

The colony morphology and cell morphology are shown in FIG. 1 and FIG. 2. The results show that after incubation on LB solid culture medium at 37° C. for 24 hours, the colonies appeared yellow, with smooth surfaces, circular shapes, and regular edges, typically with a diameter of approximately 0.5 to 0.6 mm.

Figure 3A:
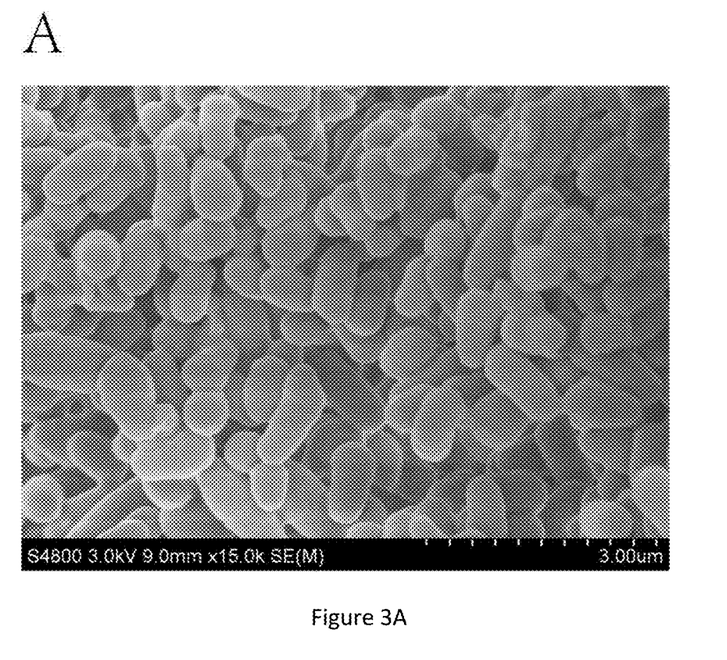
FIG. 3A shows the scanning electron microscopy images of Glutamicibacter sp. Eg-H grown in LB liquid medium without bifenthrin.
Figure 3B:
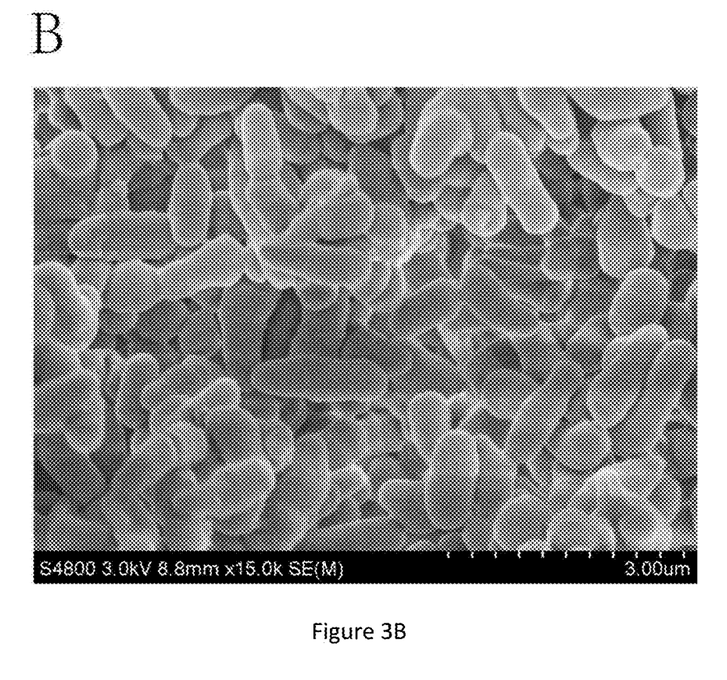
FIG. 3B shows the scanning electron microscopy images of Glutamicibacter sp. Eg-H grown in LB liquid medium with 20 mg/L of bifenthrin

FIG. 3A and FIG. 3B is a scanning electron microscope image, showing the cell morphology of Glutamicibacter sp. Eg-H grown in liquid LB culture medium with and without 20 mg/L bifenthrin, respectively. Figure A and FIG. 3B reveal that in the absence of bifenthrin, the cells have a shorter shape, while the presence of bifenthrin results in elongated cells.

Glutamicibacter sp. Eg-H is a Gram-positive bacterium with a growth temperature range of 15 to 40° ° C. (optimal growth at) 30° ° C., a NaCl tolerance range of 0 to 10% (w/v) (optimal growth at 2%), and a pH growth range of 5.0 to 10.0 (optimal growth at pH 8).

1.3 Lipid, Fatty Acid, and Quinone Profiles of the Strain

Using a 5% (v/v) inoculum, an OD600 value of 0.8 of Glutamicibacter sp. Eg-H seed liquid was inoculated into LB liquid culture medium. The culture was shaken at 37° C. and 180 rpm for 12 hours (fatty acid measurements require the use of TSB culture medium). The cell suspension was then centrifuged at 4000 rpm for 15 minutes. The collected wet bacterial cells were sent to Beijing Biogenro Biotechnology Co., Ltd. for the determination of lipids, fatty acids, and quinones. The specific experimental steps are as follows:

(1) Polar Lipid Determination

Take 100 mg of freeze-dried bacterial cells and place them in 1 ml of 0.3% NaCl. Grind for 10 minutes, transfer the crushed cells into a 50 mL organic solvent screw-cap centrifuge tube using 10 mL of methanol. Heat in a water bath for 5 minutes, then add 3 mL of 0.3% w/v NaCl solution and 5 mL of chloroform. Invert the tube for 5 minutes, and then centrifuge at 4000 rpm for 5 minutes to remove cell residues and the upper aqueous phase. Collect the chloroform layer. Add 5 mL of 0.3% NaCl solution and 5 mL of chloroform, invert the tube for 5 minutes, and centrifuge at 4000 rpm for 5 minutes. Discard the lower aqueous phase. Dry the chloroform layer at 45° C. The dried polar lipids were re-dissolved in approximately 0.1 mL chloroform/methanol (2:1, v/v) and set aside. Spot a small amount on a 10 cm×10 cm silica gel plate (Art 5554, DC-Alufolien Kieselgel 60F 254, Merck) using a capillary tube. Develop the plate in a vertical chamber using the first mobile phase (chloroform:methanol:water=65:25:4, v/v) for about 25 minutes. Remove the plate, allow it to air dry, and rotate it 90 degrees. Develop the plate using the second mobile phase (chloroform:methanol:acetic acid:water=80:12:15:4, v/v) for about 30 minutes. After drying, visualize the plate. Prepare the following staining solutions:

A: Dragendorff Reagent (D Reagent)

Solution A: Dissolve 1.7 g of bismuth nitrate in 100 mL of 20% acetic acid. Solution B: Dissolve 40 g of potassium iodide in 100 ml of distilled water. Prepare D reagent by sequentially adding 3.5 mL of solution A to 5 mL of solution B, 20 ml of acetic acid, and 50 mL of distilled water.

B: Ninhydrin Reagent (N Reagent)

Dissolve 0.4 g of ninhydrin in 100 ml of water-saturated n-butanol.

C: Anisaldehyde Reagent (A Reagent)

Mix 270 mL of 95% ethanol, 15 mL of concentrated sulfuric acid, 15 ml of p-anisaldehyde, and 3 mL of acetic acid.

D: Dittmer and Lester Reagent (P Reagent)

Solution A: Weigh 1.6 g of ammonium molybdate and dissolve it in 12 mL of water. Solution B: Add 1 mL of liquid mercury to 4 mL of concentrated hydrochloric acid and then to 8 mL of solution A. Mix thoroughly and shake for 30 minutes. Filter. The remaining solution A was added to 20 mL of concentrated sulfuric acid, and all of solution B, cooled and stored at 4° C. Before use, dilute the storage solution with water in a 1:3 (v/v) ratio to make the staining solution, which should be amber in color. For intense staining, add 2.5 mL of concentrated sulfuric acid to 100 ml of the staining solution.

E: Phosphomolybdic Acid Reagent

Dissolve 10 g of phosphomolybdic acid in 95% ethanol.

Stain with D reagent without heating; it specifically stains PC, PE, and PME. They appear as orange spots on a yellow background. Stain with N reagent and heat at 60-70° C. for 4-5 minutes; PE, PME, and some unknown phospholipids with glucosamine appear as red spots. Stain with A reagent, and heat at 65-70° C. for 10-15 minutes. Under these conditions, phospholipids with sugars or PIMS will appear as yellow-green spots. Stain with P reagent without heating; all phospholipids and P reagent will appear as blue spots. Stain with L phosphomolybdic acid reagent at 70° C. for 5-15 minutes; all polar lipids will appear as gray-brown spots on a yellow-green background.

(2) Fatty Acid Determination

Scrape an appropriate amount of the culture (about 40 mg) from the surface of the culture medium with an inoculation loop and place it in a screw-cap glass tube. Add 1 mL of saponification reagent and shake for 5-10 seconds. Tighten the cap and heat in a boiling water bath for 5 minutes. Remove and shake for 5-10 seconds, then retighten the cap and continue boiling for 25 minutes. After the sample tube has cooled, add 2 ml of methylation reagent. Secure the cap tightly, shake for 5-10 seconds, then control the temperature carefully at 80±1° C. for 10 minutes. Finally, cool in an ice bath. This step requires precise temperature and time control to avoid damaging hydroxy acids and cyclic fatty acids.

In the cooled sample tube, add 1.25 ml of extraction reagent, shake slowly for about 10 minutes, add a few drops of saturated sodium chloride solution to make the separation more distinct, and then collect the upper organic phase. Add 3 mL of 1.18% sodium hydroxide solution to the remaining organic phase, shake slowly for about 5 minutes, and add a few drops of saturated sodium chloride solution (the purpose is to make the separation more distinct). Two-thirds of the upper organic phase was collected and placed in a gas chromatography sample bottle.

Analysis of fatty acids was carried out using high-performance gas chromatography (HP6890, Hewlett Packard) equipped with a split/splitless injector, a flame ionization detector (FID), and HP gas chromatography workstation software (HP CHEMSTATION ver A 5.01). The chromatographic column used was an Ultra-2 column, 25 m in length, 0.2 mm inner diameter, and 0.33 μm film thickness. The column temperature program was as follows: initial temperature of 170° C., increasing at a rate of 5° C./min to 260° C., followed by an increase at a rate of 40° C./min to 310° C., holding for 1.5 minutes. The injector temperature was set at 250° C. Hydrogen was used as the carrier gas at a flow rate of 0.5 mL/min. The instrument was operated in the split mode (split ratio 100:1). The injection volume was 2 μL. The detector temperature was set at 300° C. The hydrogen gas flow rate was 30 mL/min, and the air flow rate was 216 mL/min. An additional gas (nitrogen) flow rate was 30 mL/min. Calibration standards were prepared using MIDI Calibration Mix 1 (MIDI, Inc.).

(3) Quinone Determination

Dry the wet bacterial cells obtained from the −80° C. freezer for 3 days. Take approximately 100 mg of freeze-dried cells and add 40 ml of a chloroform/methanol (2:1) solution in the dark. Shake on a magnetic stirrer for 10 hours. Filter the solution to collect the filtrate with filter paper. Evaporate the filtrate under reduced pressure at 40° C. Redissolve the dried residue in a small amount (1-2 mL) of acetone, and spot it in a long strip on a GF254 silica gel plate (Qingdao Marine Chemical Factory, 100 mm×200 mm). Use xylene as the elution agent and elute for approximately 20 minutes Remove the plate and allow it to air dry. Observe under a 254 nm UV lamp. The quinone band appears as a dark brown band under a green fluorescent background at an Rf value of 0.4 to 0.5. Scrape the target band and dissolve it in 1 mL of acetone. Then, use a pipette tip with a cotton plug to remove the silica gel. Collect the filtrate (which can be concentrated to 200 μl to 300 μL) to obtain the acetone solution of quinone components. Store this solution in the dark at 4° C.

The determination of quinones was performed using a reversed-phase high-performance liquid chromatography method. The high-performance liquid chromatograph used was an HP-1050 (Hewlett Packard). The reversed-phase HPLC column was C18 (ODS 5 μm, 250 mm×4.6 mm, I.D.). The mobile phase consisted of methanol (analytical grade) and isopropanol (analytical grade) in a 2:1 solution. The flow rate was 1.00 mL/min. The column temperature was maintained at 40° C. Detection was performed at 240 nm and 270 nm. An HP CHEMSTATION workstation was used for analysis and data recording. The quinone types of the experimental strain were analyzed based on the relationship between different quinone components and elution time under standard conditions, with reference to control strains.

Figure 4:
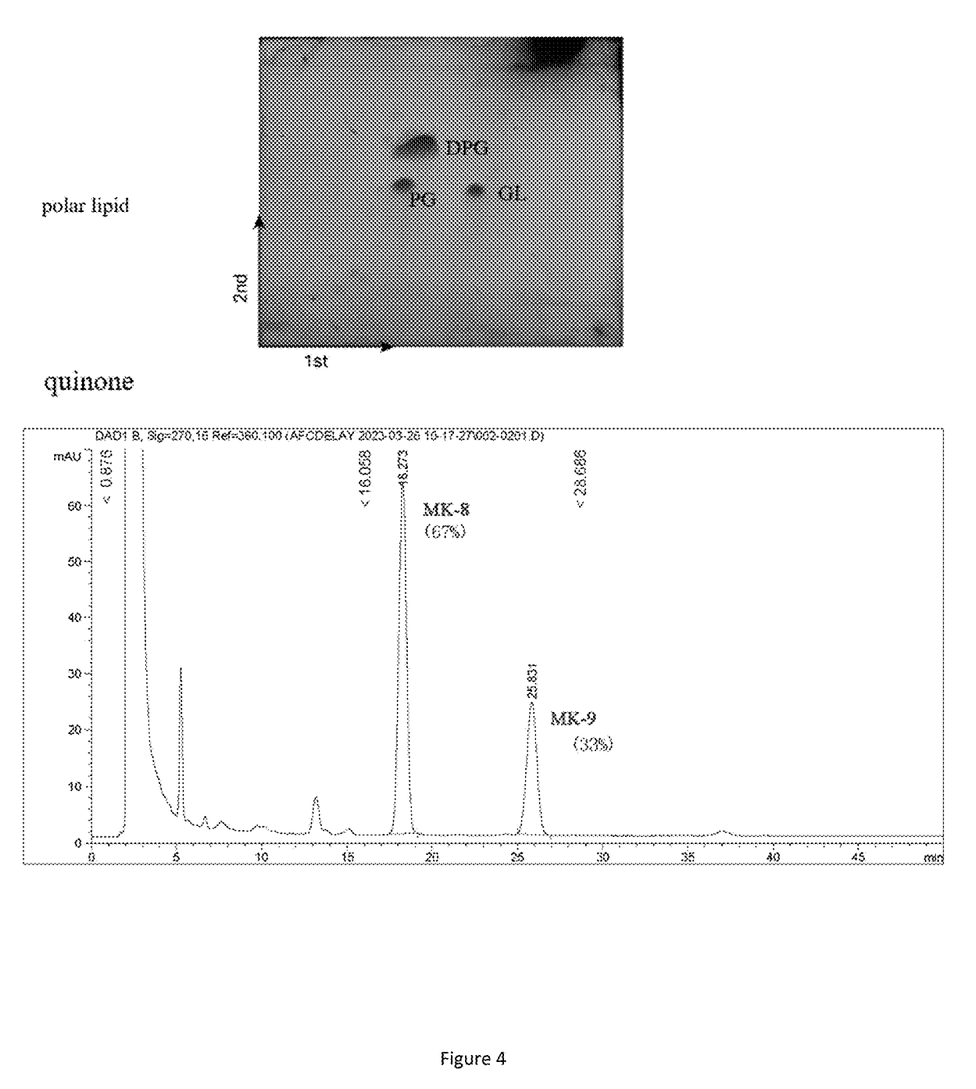
FIG. 4 shows the polar lipid profile and respiratory quinone phase image of Glutamicibacter sp. Eg-H.

In summary, the results of the cell component analysis are shown in FIG. 4. The polar lipids of the whole cell are composed of diphosphatidylglycerol (DPG), phosphatidylglycerol (PG), and glycolipids (GL). The major fatty acids were Anteiso-C15:0 (51.7%), C16:0 (16.4%), Anteiso-C17:0 (10.0%), Iso-C16:0 (9.6%). The major quinones are MK-8 and MK-9.

Example 2: Identification of Glutamicibacter sp. Eg-H via 16S rRNA Classification Perform molecular biology identification on Glutamicibacter sp. Eg-H from Example 1, the 16S rRNA gene was amplified by PCR. The PCR process used the following primers, reaction system, and conditions: Forward primer 27F sequence (5'-3'): AGAGTTTGATCCTGGCTCAG (as shown in SEQ ID NO: 2). Reverse primer 1492R sequence (5'-3'): GGTTACCTTGTTACGACTT (as shown in SEQ ID NO: 3). The PCR reaction mixture (20 μL) contained 1 μL of DNA template, 1 μL of primer 27F, 1 μL of primer 1492R, 10 μL of 2× Taq PCR StarMix, and 7 μL of ddH$_2$O. The reaction conditions were set as follows: Initial denaturation at 94° C. for 4 min; Denaturation at 94° C. for 30 s; Annealing at 55° C. for 30 s; Extension at 72° C. for 2 min; this cycle was repeated 30 times, and a final extension was carried out at 72° C. for 10 min.

Figure 5:
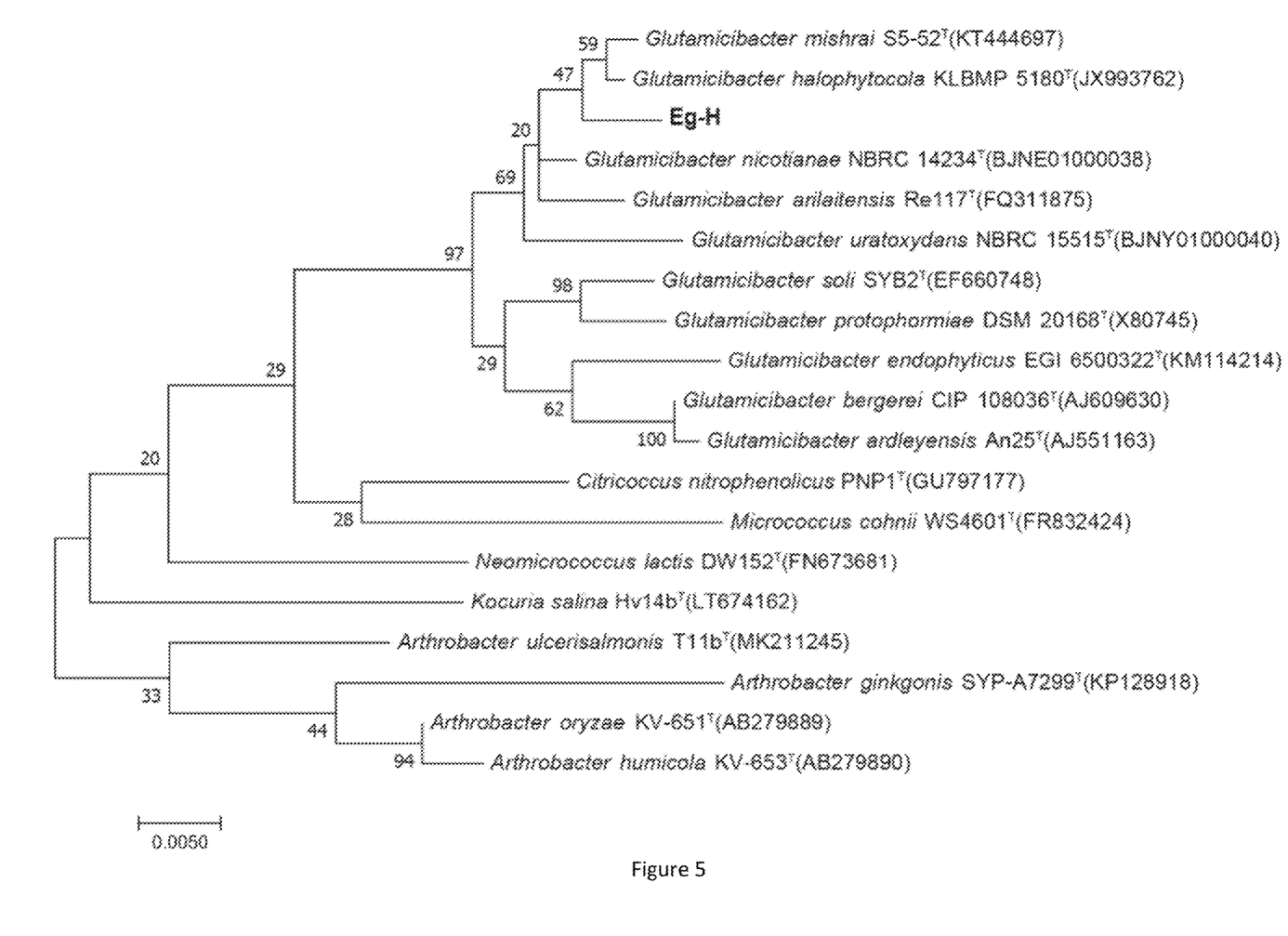
FIG. 5 shows a phylogenetic tree constructed based on the 16S rRNA gene sequences of Glutamicibacter sp. Eg-H and other type strains from the Glutamicibacter genus. The numbers at branch nodes represent repetition proportions out of 1000 replicates, with values exceeding 50% displayed at the nodes.

The sequencing results showed that the full length of the 16S rRNA gene sequence was 1414 bp (as shown in SEQ ID NO: 1). The sequence was uploaded to EzBioCloud for online alignment analysis, and high similarity mode strains' 16S rDNA sequences were downloaded. A phylogenetic tree was constructed using MEGA6.1 software through the Maximum-Likelihood method. As depicted in FIG. 5, Glutamicibacter sp. Eg-H formed a distinct branch and clustered together with model strains of the Glutamicibacter genus. The two closest phylogenetically related model strains on the adjacent branch had 16S rRNA gene sequence similarities of 98.93% and 98.16% with Glutamicibacter sp. Eg-H, and they were Glutamicibacter mishrai S5-52$^T$ and Glutamicibacter halophytocola KLBMP 5180$^T$.

Example 3: Genomic Analysis of a Novel Strain of Glutamicibacter

Following the pure cultivation of Glutamicibacter sp. Eg-H, a combined approach using third-generation PacBio and second-generation Illumina high-throughput sequencing technologies was employed to perform whole-genome sequencing. The genomic features were predicted and analyzed, and comparative genomic analysis was conducted against other known species within the Glutamicibacter genus.

Figure 6:
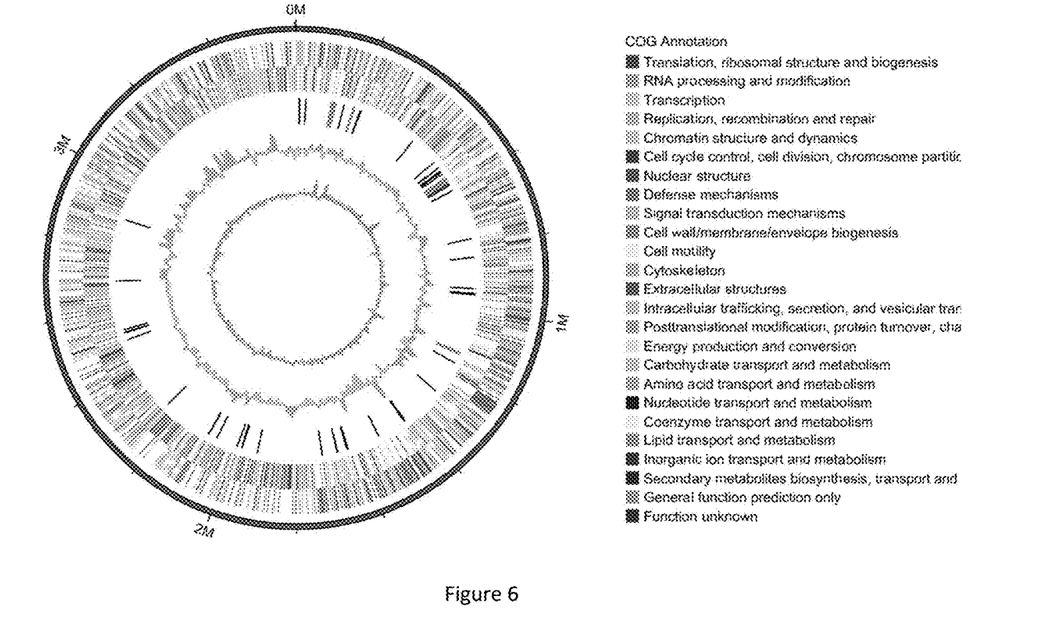
FIG. 6: shows a circular genome map of the assembled genome sequence for Glutamicibacter sp. Eg-H, aligned with predicted coding gene results. The outermost circle shows genome sequence coordinates. From outer to inner circles, the elements are: genes on the forward strand, genes on the reverse strand, ncRNA markers (black represents tRNA, red indicates rRNA), GC content (orange shows above average, blue indicates below average), and GC skew (measuring the relative content of G and C, utilized to indicate start and end points in circular chromosomes; GC skew=(G-C)/(G+C), where purple indicates above 0, and orange is below 0).

For DNA extraction, Glutamicibacter sp. Eg-H was collected when the OD$_{600}$ value of the bacterial culture in LB liquid medium reached 0.8. Total DNA was extracted and sent to Guangzhou GENE DENOVO Biological Technology Co., Ltd. for genome sequencing. Predictive analysis of the genome-encoded genes revealed a total genome length of 3,189,534 bp, with 3362 genes, an average gene length of 948.70 bp, 19 rRNA sequences, 64 tRNA sequences, 1 sRNA sequence, and a GC content of 55.78%. FIG. 6 represents the genome prediction.

Functional annotation of Glutamicibacter sp. Eg-H's genome data, based on Gene Ontology (GO) classification, indicated that all genes in the strain could be categorized into three main groups: those involved in biological processes, cellular components, and molecular functions. In terms of genes associated with biological processes, the majority were related to cell processes (2295), metabolic processes (2085), single-organism processes (2069), localization (723), response to stimulus (654), biological regulation (647), cellular component organization or biogenesis (597), and regulation of biological processes (587). For genes annotated with molecular functions, a larger number were linked to catalytic activity (1952), binding activity (1532), transporter activity (550), nucleic acid binding transcription factor activity (264), and structural molecule activity (106). In the category of cellular components, the predominant genes were associated with cells (1403), cell parts (1401), membranes (1011), membrane parts (632), macromolecular complexes (individuals), organelles (213), and organelle parts (164).

Functional classification of proteins in Glutamicibacter sp. Eg-H's genome data using COG (Clusters of Orthologous Groups) revealed 369 genes involved in amino acid transport and metabolism (category E), 234 genes involved in transcription (category K), and 215 genes associated with carbohydrate transport and metabolism (category G).

CAZyme (Carbohydrate-Active Enzymes) annotation of Glutamicibacter sp. Eg-H indicated that the most abundant categories of sugar-active enzymes were glycosyl transferases (210 genes) and glycoside hydrolases (126 genes).

Comparative genomic analysis between Glutamicibacter sp. Eg-H and five known model strains of Glutamicibacter (as shown in Table 1) indicated that both DNA-DNA hybridization (DDH) values and Average Nucleotide Identity (ANI) values were lower than the defined thresholds used to distinguish different species (dDDH <70%, ANI <96%).

TABLE 1

Genomic sequence similarity between *Glutamicibacter* sp. Eg-H and reference strains

| Contrast strain | dDDH(%) | ANI(%) |
|---|---|---|
| *Glutamicibacter mishrai* S5-52[T] | 25.5 | 82.78 |
| *Glutamicibacter halophytocola* KLBMP 5180[T] | 24.6 | 81.99 |
| *Glutamicibacter nicotianae* NBRC 14234[T] | 21.3 | 78.73 |
| *Glutamicibacter arilaitensis* Re117[T] | 21.3 | 78.49 |
| *Glutamicibacter uratoxydans* NBRC 15515[T] | 20.2 | 76.59 |

Example 4: Physiological and Biochemical Experimental Identification

Fresh pure cultures of Glutamicibacter sp. Eg-H were sent to Beijing Biogenro Biotechnology Co., Ltd. Various biochemical identification methods were employed, including API 20NE, API ZYM, API 50 CH (bioMérieux), the Biolog GEN III test kit (following the manufacturer's instructions), and bacterial biochemical microtest tubes (provided by Hangzhou Tianhe Microbial Reagents Co., Ltd.). These tests were conducted to obtain unique carbon source utilization and enzymatic characteristics of this bacterium. The experimental results were compared with the five closest bacterial strains in the phylogenetic tree, as shown in Table 2. Based on the phylogenetic, phenotypic, and physiological biochemical data, it was possible to further classify this strain as a novel species within the Glutamicibacter genus, tentatively named Glutamicibacter sp. Eg-H.

Glutamicibacter sp. Eg-H has been preserved and deposited at the China Center for Type Culture Collection (CCTCC) on Sep. 16, 2022. The preservation site is Wuhan University, Wuhan, China, and the preservation identification number is CCTCC NO: M 20221445.

TABLE 2

Distinctive features for distinguishing *Glutamicibacter* sp. Eg-H from closely related strains

| Characteristic | strain 1 | strain 2 | strain 3 | strain 4 | strain 5 | strain 6 |
|---|---|---|---|---|---|---|
| pH | 5-10 | 5-11 | 4-10 | 6-10 | 5-11 | 7-8 |
| NaCl % (m/v) | 0-10 | 0-12 | 0-13 | 0-7 | 0-10 | 0-10 |
| Motility | − | − | − | − | − | − |
| Oxidase | − | + | + | ND | − | ND |
| Catalase | + | + | + | ND | + | ND |
| Enzymology Character (API ZYM) | | | | | | |
| Esterase (C4) | w | + | − | + | − | + |
| Lipase (C8) | w | + | + | + | − | + |
| Lipase (C14) | − | − | + | + | − | − |
| Tyrosine Arylaminidase | + | − | − | + | + | + |
| Cystine Arylaminidase | + | − | − | − | − | + |
| Acid Phosphatase | − | + | − | + | − | + |
| α-Galactosidase | − | + | + | − | − | − |
| β-Galactosidase | − | + | − | − | + | − |
| β-Glucuronidase | − | + | − | − | − | − |
| α-Glucosidase | w | + | + | + | + | + |
| Carbon Source Fermentation (API 50CH) | | | | | | |
| D-Arabinose | − | − | − | − | − | − |
| L-Arabinose | + | + | + | + | + | − |
| D-Xylose | + | + | + | + | + | − |
| L-Xylose | − | − | − | − | − | − |
| D-Arabinose alcohol | − | + | − | − | − | − |
| D-Lactose | + | + | − | + | − | − |
| D-Glucose | + | + | + | + | − | + |
| D-Fructose | + | + | − | + | − | + |
| D-Mannose | − | + | − | − | − | − |
| L-Sorbose | − | − | − | − | − | − |
| Rhamnose | + | + | + | − | − | − |
| Salicin | − | − | − | − | − | − |
| Inositol | + | + | + | − | − | − |
| D-Mannitol | − | + | − | + | − | − |
| D-Sorbitol | − | − | − | − | − | − |
| Methyl-α-D-fucopyranoside | − | − | + | − | − | − |
| Methyl-α-D-galactopyranoside | − | + | + | − | + | − |
| N-Acetylglucosamine | − | + | + | − | + | + |
| Amygdalin | − | + | − | + | − | − |
| Arbutin | − | + | − | − | + | − |
| Escarin Citrate | + | + | − | + | + | − |
| Salicin | − | − | − | + | + | − |
| D-Cellobiose | + | + | + | + | + | − |
| D-Maltose | + | + | + | + | + | + |
| D-Lactose | − | − | + | + | + | − |
| D-Melibiose | − | + | + | − | − | − |
| D-Saccharose | + | + | + | − | + | + |
| D-Trehalose | − | − | − | − | + | − |
| Inulin | + | + | + | − | − | − |
| D-Melezitose | − | + | + | − | − | − |
| D-Raffinose | + | + | + | − | − | − |
| Glycogen | + | + | + | + | + | − |
| Xylitol | + | + | + | + | + | − |
| Gentiobiose | − | − | − | − | − | − |
| D-Turanose | − | − | − | + | + | − |
| D-Turanose | − | + | + | − | + | − |
| D- tagatose | − | + | − | − | − | − |
| L-Fucose | − | + | − | − | − | − |
| D-Ribitol | + | + | + | + | + | − |
| 5-Ketoglucose salt API 20NE | − | − | − | − | − | − |
| Nitrate reduction | − | − | + | + | − | + |
| Nitrate reduction to nitrogen | − | − | − | − | − | − |
| Urea | + | + | + | − | − | + |
| Hydrolysis of ferric citrate | − | − | − | − | − | − |
| Hydrolyzed gelatin (bovine source) | + | + | + | + | + | + |
| Hydrolysis of 4-nitrophenyl-β-D-pyranoside | + | + | + | − | + | − |
| Assimilation of L-arabinose | + | + | + | + | + | + |
| Assimilation of D-mannose | w | + | + | + | + | + |
| Assimilation of D-mannitol | w | + | + | − | − | − |
| Assimilation of N-acetylglucosamine | − | − | − | − | − | + |
| Assimilation of salicylic acid | − | − | − | − | − | + |
| Assimilation of malic acid | + | + | + | + | − | + |
| Assimilation of sodium citrate | + | + | + | + | − | + |
| Carbon source utilization assay | | | | | | |
| Cyclodextrin | + | − | + | − | − | − |
| Tween 40 | − | − | + | + | + | + |
| D-Arabitol | + | − | − | − | − | − |
| D-Fructose | + | + | + | + | − | + |
| D-Gluconic acid | + | − | + | − | − | − |
| α-D-Glucose | + | − | + | + | − | − |
| α-D-Lactose | − | − | − | − | − | − |

TABLE 2-continued

Distinctive features for distinguishing *Glutamicibacter* sp. Eg-H from closely related strains

| Characteristic | strain 1 | strain 2 | strain 3 | strain 4 | strain 5 | strain 6 |
|---|---|---|---|---|---|---|
| Maltose | + | − | − | − | − | − |
| D-Mannitol | − | + | + | + | − | − |
| D-Mannose | − | + | − | + | − | − |
| D-Melibiose | + | − | + | − | − | − |
| D-Ribose | + | − | + | + | + | + |
| D-Sorbitol | − | + | + | − | − | − |
| Sucrose | + | − | + | − | − | − |
| turanose | w | − | + | + | + | + |
| L-Lactic acid | + | − | + | − | + | + |
| D-Malic acid | − | − | − | − | − | − |
| L-Malic acid | + | − | − | − | − | − |
| Propionic acid | + | − | − | − | − | − |
| D-alanine | + | − | − | − | − | − |
| L-alanine | + | − | + | − | − | − |
| Glutamic acid | + | − | − | + | − | − |
| pyroglutamic acid | + | − | − | + | − | + |
| Serine | + | − | − | − | − | + |
| Glycerol | + | + | + | + | + | + |
| Inosine | + | − | + | − | − | − |

Note:
+: Positive;
−: Negative;
w: Weak positive;
Data for strains 2-6 are from the reference (Das Lipika, Deb Sushanta, Das Subrata K. *Glutamicibacter mishrai* sp. nov., isolated from the coral Favia veroni from Andaman Sea. Archives of microbiology, 2020, 202(04): 733-745).
Strain 1: *Glutamicibacter* sp. Eg-H;
Strain 2: *Glutamicibacter mishrai* S5-52$^T$;
Strain 3: *Glutamicibacter halophytocola* KLBMP 5180$^T$;
Strain 4: *Glutamicibacter nicotianae* NBRC 14234$^T$;
Strain 5: *Glutamicibacter arilaitensis* Re117$^T$; S
train 6: *Glutamicibacter uratoxydans* NBRC 15515$^T$.

Example 5: Application of Glutamicibacter sp. Eg-H in the Degradation of Bifenthrin Glutamicibacter sp. Eg-H seed liquid with $OD_{600}$ value of 0.8 was added to MSM medium containing bifenthrin (6 mg/L bifenthrin, $(NH_4)_2SO_4$ 0.2%, $MgSO_4 \cdot 7H_2O$ 0.02%, $CaCl_2$) 0.001%, $FeSO_4 \cdot 7H_2O$ 0.0001%, $Na_2HPO_4 \cdot 12H_2O$ 0.15%, $KH_2PO_4$ 0.15%) at a 5% (v/v) inoculation rate. This culture was incubated at a constant temperature of 37° C. with agitation at 200 rpm. Samples were collected at intervals of 12 hours, 24 hours, 36 hours, 48 hours, and 60 hours. Measure its $OD_{600}$ value and plot the growth curve of the strain under the condition with bifenthrin as the sole carbon source. The control group was without the addition of Glutamicibacter sp. Eg-H, whereas the test group included Glutamicibacter sp. Eg-H. The remaining bifenthrin content was analyzed using Agilent gas chromatography. The methods are as follows:

(1) Sample Preprocessing:

Take 10 ml of the culture and add an equal volume of ethyl acetate for extraction; Vortex for 5 minutes, then let it separate; Add 1.5 g of anhydrous sodium sulfate to saturation; Centrifuge at 4000 rpm for 10 minutes; Transfer the upper organic phase to a new centrifuge tube; Add 10 ml of ethyl acetate to the residual lower liquid in the original tube; Repeat the previous steps; Combine the organic phases from both extractions; Vortex for 5 minutes; Take 1 mL and evaporate using a nitrogen blower for 15 minutes until dry; Bring the volume to 10 mL with n-hexane; Filter through a 0.22 μm organic phase filter membrane; Store in a chromatography vial for gas chromatograph analysis.

(2) Gas Chromatography:

Column: HP-5 (30 m×0.25 mm, 0.25 μm), ECD detector; Initial column temperature: 40° C. for 1 minute; Increase at 15° C. per minute to 280° C.; Detection temperature: 300° C.; Injection port temperature: 275° C.; Injection volume: 1 μL; The degradation rate was calculated using the formula: Degradation rate=(1−test group residue/control group residue)×100%.

Figure 7:
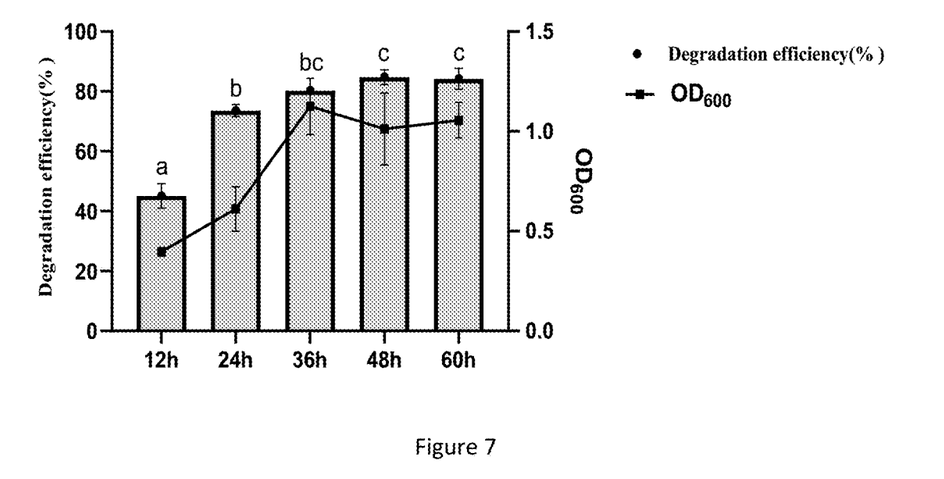
FIG. 7 shows the biomass of Glutamicibacter sp. Eg-H and the degradation efficiency of bifenthrin over various cultivation periods.

As shown in FIG. 7, at 36 hours of cultivation, the $OD_{600}$ value of the bacterial culture reached its maximum at 1.13 (as shown in Table 3). Afterward, it entered a growth plateau phase, with a slight decrease in OD600 value to 1.012 at 48 hours, followed by minor fluctuations. Simultaneously, at 36 hours, Glutamicibacter sp. Eg-H achieved an 80.30% degradation efficiency of 6 mg/L bifenthrin, and at 48 hours, the degradation efficiency reached a maximum of 84.75%.

TABLE 3

Determination of bifenthrin degradation with different duration

| | | 12 h | 24 h | 36 h | 48 h | 60 h |
|---|---|---|---|---|---|---|
| Eg-H strain before inoculation | OD | 0 | 0 | 0 | 0 | 0 |
| | degradation rate | 0% | 0% | 0% | 0% | 0% |
| Eg-H strain after inoculation | OD | 0.397 | 0.611 | 1.125 | 1.012 | 1.056 |
| | degradation rate | 45.118% | 73.621% | 80.300% | 84.753% | 84.202% |

Example 6: Use of Glutamicibacter sp. Eg-H for the Degradation of Different Concentrations of Bifenthrin Glutamicibacter sp. Eg-H seed liquid with an $OD_{600}$ of 0.8 were inoculated at 5% (v/v) into MSM culture media containing bifenthrin at concentrations of 6 mg/L, 20 mg/L, 60 mg/L, 100 mg/L, and 200 mg/L. The cultures were incubated at 37° C. with agitation at 200 rpm for 48 hours. Each group had three replicates. Quantitative analysis of the strain's degradation capability was conducted using gas chromatography, following the same sample preparation and gas chromatography methods described in Example 5.

Figure 8:
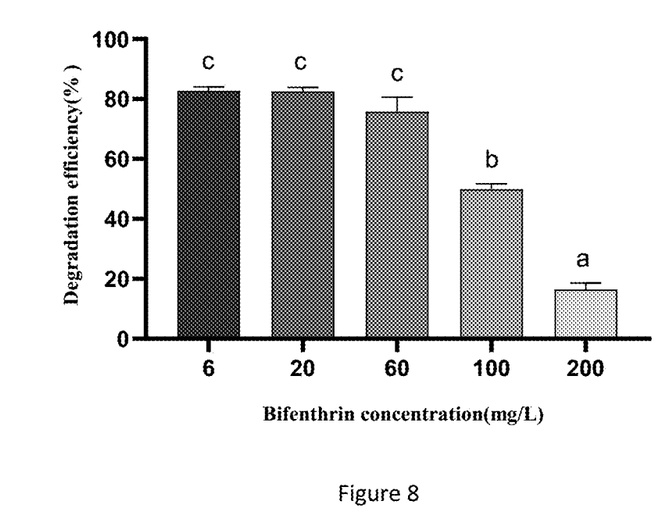
FIG. 8 shows the degradation efficiency of Glutamicibacter sp. Eg-H at different concentrations of bifenthrin.

As shown in FIG. 8, when the concentration of bifenthrin in the culture medium was less than or equal to 60 mg/L, Glutamicibacter sp. Eg-H exhibited a high degradation efficiency, ranging between 75.78% and 85%. However, as the concentration of bifenthrin increased to 100 mg/L, there was a significant decrease in the degradation rate (P<0.05) to 49.89% (as shown in Table 4). Furthermore, when the culture medium contained a high concentration of 200 mg/L bifenthrin, Glutamicibacter sp. Eg-H was able to maintain a degradation rate of 16.49%.

TABLE 4

Determination of bifenthrin degradation at different concentrations

| degradation rate | 6 mg/L | 20 mg/L | 60 mg/L | 100 mg/L | 200 mg/L |
|---|---|---|---|---|---|
| Repeat 1 | 84.187% | 81.332% | 78.552% | 47.955% | 17.199% |
| Repeat 2 | 81.440% | 84.010% | 70.148% | 51.647% | 18.197% |
| Repeat 3 | 82.406% | 82.211% | 78.653% | 50.073% | 14.084% | sp. Eg-H

Glutamicibacter sp. Eg-H seed liquid with an $OD_{600}$ of 0.8 was inoculated at 5% (v/v) into MSM culture medium containing 20 mg/L bifenthrin. The culture was incubated for 48 hours at 37° C. with agitation at 200 rpm. The detection of bifenthrin and its degradation products in the culture medium was performed using the following methods:

(1) Sample Preparation: The sample preparation process was the same as described in Example 5.

(2) Target compound determination and analysis using gas chromatography-mass spectrometry (GC-MS): Chromatographic conditions included an HP-5 MS capillary column (30 m×0.25 mm, 0.25 μm), an injection port temperature of 250° C. Heating program: initial temperature of 160° C. held for 5 minutes, increased at a rate of 10° C./min to 200° C., held for 1 minute, and finally increased at a rate of 10° C./min to 280° C., held for 8 minutes. Helium gas was used as the carrier gas at a flow rate of 1.5 mL/min. Mass spectrometry conditions included electron ionization, an ion source temperature of 230° C., and an electron energy of 70 eV.

Figure 9A:
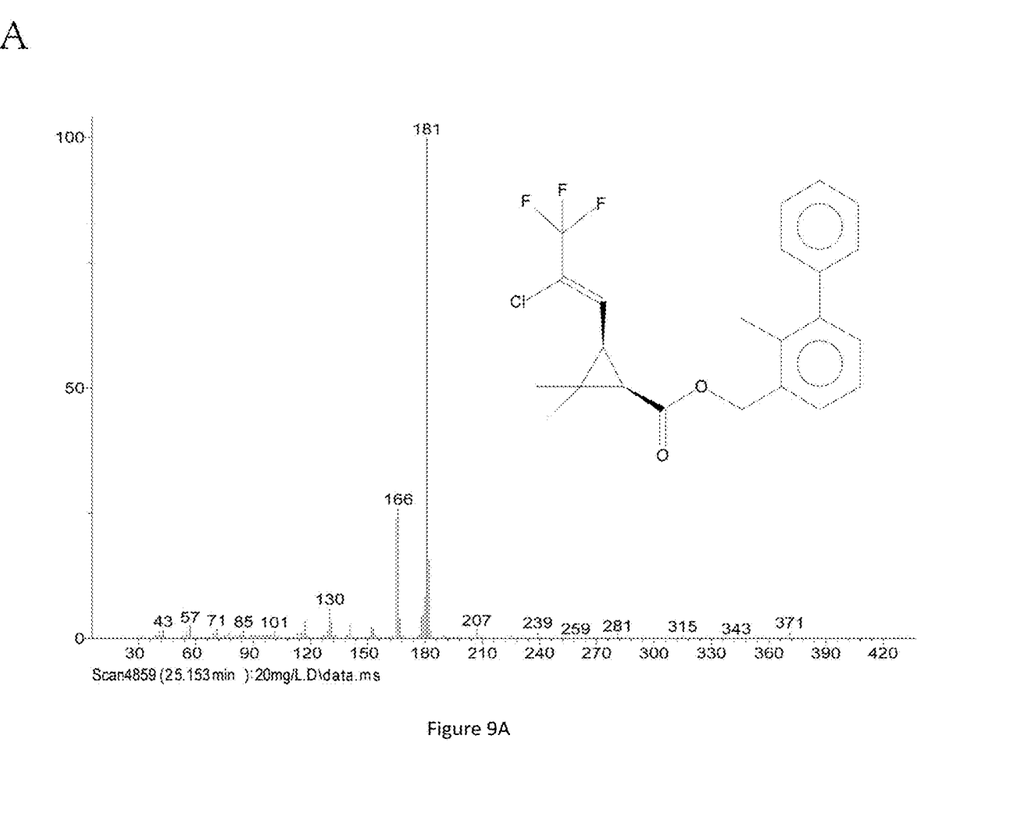
FIG. 9A shows the GC-MS spectrum analysis of bifenthrin.
Figure 9B:
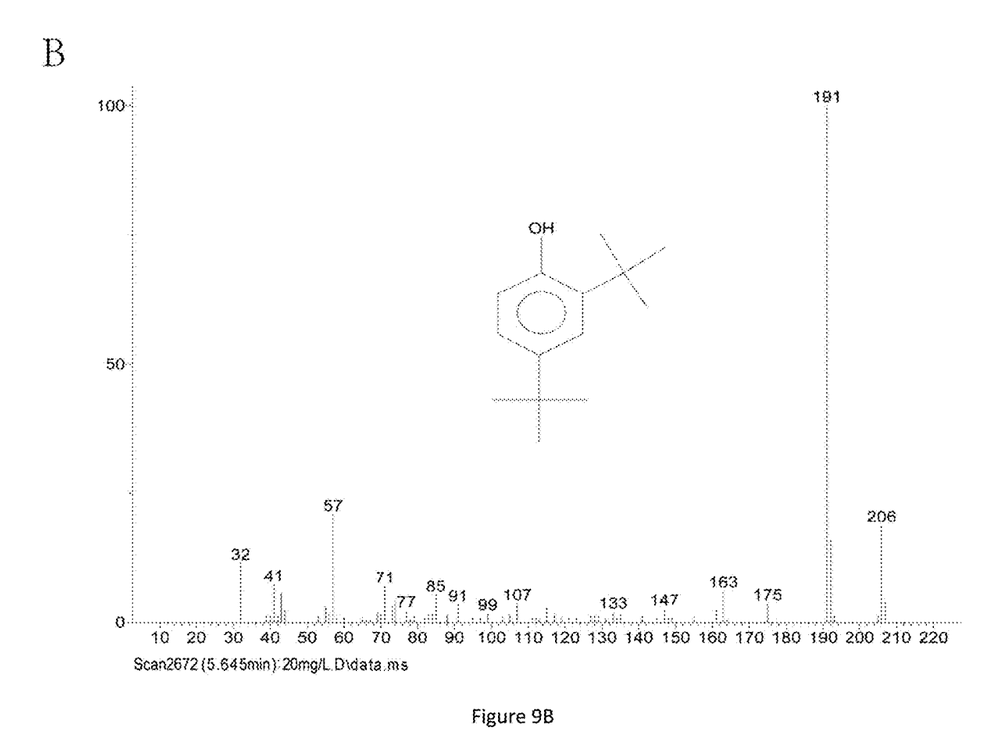
FIG. 9B shows the GC-MS spectrum analysis of bifenthrin metabolic products by Glutamicibacter sp. Eg-H.

The results showed that bifenthrin had a retention time of 25.153 minutes. Upon retrieval and comparison in the NIST database, the main differential peak, after removing impurity peaks such as siloxane, was identified as 2,4-di-tert-butylphenol. Based on the GC-MS mass spectra of bifenthrin and its metabolic products (FIG. 9A and FIG. 9B), it was observed that the peak had a retention time around 15.614 minutes, a NIST database match similarity of 95.08%, and a retention index of 1510.

Example 8: Toxicity Testing of 2,4-Di-tert-butylphenol, a Bifenthrin Degradation Product A stock solution of 2,4-di-tert-butylphenol (purchased from Beijing Solarbio Science & Technology Co., Ltd., HPLC≥99%) was prepared following the preparation method for bifenthrin stock solution. This stock solution was added to sterile artificial food at a final concentration of 100 mg/L. This food was used to feed 30 healthy 4-5 aged *E. grisescens* larvae. The control group was fed normal sterile artificial food.

Figure 10:
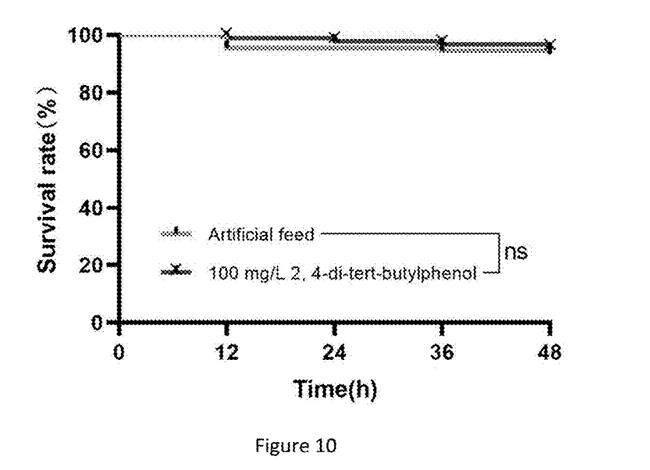
FIG. 10 shows the toxicity test results of the bifenthrin metabolic product, 2,4-di-tert-butylphenol, on the *E. grisescens*.

As shown in FIG. 10, 48 hours later, the survival rate of *E. grisescens* larvae fed sterile artificial food was 93.33%. In comparison, the survival rate of larvae from the sensitive strain fed with artificial food containing 2,4-di-tert-butylphenol was even higher at 94.45%. There were no statistically significant differences in the survival curves between the two groups. Therefore, this degradation product, 2,4-di-tert-butylphenol, showed little to no toxicity to the *E. grisescens* larvae.

Example 9: Composition Containing Strain Glutamicibacter sp. Eg-H

A composition containing strain Glutamicibacter sp. Eg-H was provided as a microbial agent. The microbial agent can be in the form of a liquid or solid. In the microbial agent, the live cell count of Glutamicibacter sp. Eg-H CCTCC NO: M20221445 was greater than or equal to 10^7 CFU per gram or per milliliter.

Optionally, the preparation of the liquid microbial agent involves activating Glutamicibacter sp. Eg-H CCTCC NO: M20221445 and inoculating it into LB liquid medium for cultivation.

Optionally, the solid microbial agent was in the form of freeze-dried powder containing Glutamicibacter sp. Eg-H CCTCC NO: M20221445.

Optionally, perform multi-stage activation and cultivation of *Gluconobacter* sp. Eg-H CCTCC NO: M20221445 to obtain a seed culture. Subsequently, centrifuge and wash multiple times to obtain bacterial pellets. The process includes centrifugation and repeated washing to obtain cell paste. Then, the cell paste was dissolved in a protectant, pre-frozen, and subsequently freeze-dried using a freeze-drying machine. The optional freeze-drying conditions include a temperature of −72° C., a pressure of 0.1 MPa, and the resulting live cell count was 10^7 CFU/g. The optional protectant was used at 10% of the seed solution.

Optionally, the microbial agent may also contain other excipients, such as maltodextrin and starch.

Optionally, the microbial agent can be formulated as a liquid microbial agent by adding excipients like glycerol and dimethyl sulfoxide. The live cell count was 10^7 CFU/mL.

Example 10: Application of Microbial Agent Containing Strain Glutamicibacter sp. Eg-H in the Degradation of Bifenthrin Preparation of Microbial Agent Containing Strain Glutamicibacter sp. Eg-H (Liquid Form): Glutamicibacter sp. Eg-H seed liquid with an $OD_{600}$ of 0.8 was added to LB medium at a 5% volume-to-volume (v/v) ratio and cultivated at 30° C. for 12 hours. After cultivation, the bacterial cells were collected by centrifugation at 4000 rpm for 3 minutes. The collected cells were resuspended in a 50% glycerol solution to create the liquid microbial agent. The microbial agent contains live cell counts greater than or equal to 10^7 CFU/mL.

Application of the Microbial Agent:

Following the procedure in Example 5, the liquid microbial agent was added to a bifenthrin-containing MSM culture medium at a concentration where the live cell count of Glutamicibacter sp. Eg-H reaches 10^5 CFU/mL. The culture was maintained for 60 hours, and the remaining content of bifenthrin was determined. The results show that at 36 hours, Glutamicibacter sp. Eg-H had achieved a degradation efficiency of 78.50% when degrading 30 mg/L of bifenthrin. By 60 hours, the degradation efficiency reached a maximum of 80.9%.

Example 11: Degradation of Bifenthrin in Soil Using Microbial Agent Containing Strain Glutamicibacter sp. Eg-H Preparation of Microbial Agent Containing Strain Glutamicibacter sp. Eg-H (Solid Form): In a multi-step activation culture, Glutamicibacter sp. Eg-H (CCTCC NO: M20221445) was activated to produce a seed liquid. The bacterial cells were collected by centrifugation at 4000 rpm for 3 minutes, washed with PBS three times, and the supernatant was discarded to obtain bacterial slurry. The slurry was then dissolved in a solution containing 5% (w/v) maltodextrin and other freeze-drying protectants. It was pre-frozen and then freeze-dried at −72° C. and 0.1 MPa pressure for 12 hours, using a freeze-drying machine. After freeze-drying, the solid microbial agent was obtained. The microbial agent contained live cell counts greater than or equal to 10^7 CFU/g.

One kilogram of field soil was randomly collected and divided into a control group and a test group. Both groups with bifenthrin added to the soil to achieve a final concentration of 10 mg/kg. The test group was supplemented with a 5% (mass fraction) microbial agent, which results in a live cell count of 10^8 CFU in the soil. The soil was mixed thoroughly. The experiment was carried out at room temperature, and samples were collected at 12 hours, 24 hours, 36 hours, 48 hours, and 60 hours. The remaining bifenthrin content in the soil was determined using an Agilent gas chromatograph, and degradation efficiencies were calculated.

(1) Sample Preparation: Ten grams of soil were mixed with 10 mL of distilled water, centrifuged at 4000 rpm for 5 minutes, and the supernatant was obtained. It was mixed with an equal volume of ethyl acetate, vortexed for 5 minutes, left to settle, and then saturated with 1.5 g of anhydrous sodium sulfate. After centrifuging at 4000 rpm for 10 minutes, the upper organic phase was transferred to a new centrifuge tube. The remaining lower liquid in the original centrifuge tube was treated again with 10 ml of ethyl acetate following the same steps. The organic phases from both extractions were combined and vortexed for 5 minutes, and 1 mL was drawn and dried with nitrogen. The sample was reconstituted with n-hexane to 10 mL and filtered through a 0.22 μm organic phase membrane before analysis by gas chromatography.

(2) Gas Chromatography Conditions: HP-5 column (30 m×0.25 mm, 0.25 μm), ECD detector, initial column temperature of 40° C. held for 1 minute, 15° C./min ramp to 280° C., detector temperature of 300° C., injector temperature of 275° C., and an injection volume of 1 μL. Degradation Rate Calculation: The degradation rate was calculated using the formula: Degradation rate=(1−test group residue/control group residue)×100%.

The results show that in the test group, the degradation efficiency of 10 mg/kg bifenthrin reaches 72.9% at 48 hours and a maximum of 76.7% at 60 hours.

Example 12: Microbial Fertilizer Containing Strain Glutamicibacter sp. Eg-H

A microbial fertilizer was provided that contains Glutamicibacter sp. Eg-H (CCTCC NO: M20221445) of the present disclosure. This microbial fertilizer can be applied to the degradation of bifenthrin residues in soil.

Optionally, the microbial fertilizer can be a slow-release microbial fertilizer. It may include ingredients like straw ash, diatomaceous earth, expanded vermiculite, urea, magnesium sulfate, potassium sulfate, Glutamicibacter sp. Eg-H (CCTCC NO: M20221445) microbial agent, glutinous rice starch, ammonium chloride, ammonium dihydrogen phosphate, and sodium alginate. Some magnesium sulfate and potassium sulfate, along with the microbial agent, can be compounded with glutinous rice starch, loaded into expanded vermiculite, and then mixed with other fertilizer ingredients to achieve a good slow-release effect.

Optionally, the microbial fertilizer can be a soil-conditioning microbial fertilizer. It's made from the following weight percentages of raw materials: Glutamicibacter sp. Eg-H (CCTCC NO: M20221445) microbial agent 40-45%; Potassium humate 25-30%; Amino azoles 2-3%; Yeast extract 5-6%; Chitosan 5-6%; Sodium humate 4-6%; Seaweed extract 4-6%; Composite protease 2-3%. This soil-conditioning microbial fertilizer can be used for at least one of the following purposes: (1) improving soil compaction and balancing soil structure; (2) ameliorating soil salinization and acidification; (3) degrading heavy metals and pesticide residues in soil; (4) promoting root growth, enhancing seedling vigor, increasing the disease resistance of crops, and improving fruit setting.

Example 13: Feed Containing Strain Glutamicibacter sp. Eg-H for Raising E. grisescens A feed was provided for enhancing the resistance of E. grisescens to bifenthrin. The feed contains Glutamicibacter sp. Eg-H (CCTCC NO: M20221445).

Optionally, the feed may further contain the following components: duck egg white liquid 2-5 parts, Japanese honeysuckle stem and leaf powder 1.5-2.3 parts, Chinese privet leaf powder 1-1.6 parts, sucrose 0.7-1.5 parts, honeysuckle leaf powder 1-1.8 parts, vitamin C 0.01-0.04 parts, potassium sorbate 0.001-0.005 parts, sodium ascorbate 0.008-0.04 parts, agar 1-5 parts, edible gelatin 0.1-0.6 parts, and water 150-270 parts.

Optionally, the Glutamicibacter sp. Eg-H (CCTCC NO: M20221445) in the feed was present in a range of 1-10 parts.

Although the disclosure has been disclosed in better embodiments, it was not intended to restrict the disclosure, and any person familiar with the technology may make various modifications and modifications within the spirit and scope of the disclosure, therefore, the scope of protection of the disclosure shall be as defined in the claim.

---

What is claimed is:

1. A method for degrading bifenthrin, comprising adding a microbial agent to a system containing bifenthrin; wherein the microbial agent comprises Glutamicibacter sp. Eg-H CCTCC NO: M20221445, deposited at the China Typical Culture Collection Center on Sep. 16, 2022, with deposit number CCTCC NO: M20221445.

2. The method according to claim 1, wherein the concentration of bifenthrin in the system is 6-200 mg/L.

3. The method according to claim 1, wherein the concentration of bifenthrin in the system is 5-100 mg/L.

4. The method according to claim 1, wherein the concentration of bifenthrin in the system is 5-60 mg/L.

5. The method according to claim 1, wherein an amount of inoculation of Glutamicibacter sp. Eg-H CCTCC NO: M20221445 is 2-7% v/v.

* * * * *